United States Patent [19]

Oxman et al.

[11] Patent Number: 5,145,886

[45] Date of Patent: Sep. 8, 1992

[54] RADIATION ACTIVATED HYDROSILATION REACTION

[75] Inventors: Joel D. Oxman, St. Louis Park; Larry D. Boardman, Shoreview, both of Minn.

[73] Assignee: Minnesota Mining and Manufacturing Company, St. Paul, Minn.

[21] Appl. No.: 602,411

[22] Filed: Oct. 22, 1990

Related U.S. Application Data

[62] Division of Ser. No. 354,629, May 19, 1988, abandoned.

[51] Int. Cl.$^5$ .......................... C08F 2/50; C08F 4/80; G08G 77/06; G08G 77/12
[52] U.S. Cl. ............................ 522/66; 522/99; 528/15; 528/31; 528/32
[58] Field of Search ............... 528/15, 31, 528/32; 522/66, 99

[56] References Cited

U.S. PATENT DOCUMENTS

| | | | |
|---|---|---|---|
| 3,159,662 | 12/1964 | Ashby et al. | 260/448.2 |
| 3,178,464 | 4/1965 | Pierpoint | 260/448.3 |
| 3,220,972 | 11/1965 | Lamoreaux | 260/46.5 |
| 3,313,773 | 4/1967 | Lamoreaux | 260/46.5 |
| 3,410,886 | 11/1968 | Joy | 260/448.2 |
| 3,470,225 | 9/1969 | Knorre | 260/448.2 |
| 3,567,755 | 3/1971 | Seyfried | 260/448.2 |
| 3,723,497 | 3/1973 | Baney | 524/588 |
| 3,814,731 | 6/1974 | Nitzsche | 260/46.5 |
| 4,177,341 | 12/1979 | Kreis et al. | 528/32 |
| 4,243,718 | 1/1981 | Murai et al. | 428/411 |
| 4,276,252 | 1/1981 | Kreis et al. | 264/222 |
| 4,281,093 | 7/1981 | Garden | 528/31 |
| 4,288,345 | 9/1981 | Ashby et al. | 252/431 |
| 4,510,094 | 4/1985 | Drahnak | 260/429 |
| 4,530,879 | 7/1985 | Drahnak | 528/15 |
| 4,603,215 | 7/1986 | Chandra et al. | 556/136 |
| 4,640,939 | 2/1987 | Cavezzan | 522/99 |
| 4,670,531 | 6/1987 | Eckberg | 528/15 |
| 4,699,813 | 10/1987 | Cavezzan | 427/387 |
| 4,705,765 | 11/1987 | Lewis | 502/152 |
| 4,712,092 | 12/1987 | Boldridge, Jr. | 340/365 |

FOREIGN PATENT DOCUMENTS

| | | |
|---|---|---|
| 0238033 | 8/1987 | European Pat. Off. . |
| 2367801 | 5/1978 | France . |

OTHER PUBLICATIONS

Gregory L. Geoffroy, *Organometallic Photochemistry*, pp. 201–204, 320–322 and 260, Academic Press, 1979.

*Primary Examiner*—Marion E. McCamish
*Assistant Examiner*—Susan Berman
*Attorney, Agent, or Firm*—Gary L. Griswold; Walter N. Kirn; David L. Weinstein

[57] ABSTRACT

A process for the actinic radiation-activated addition reaction of a compound containing silicon-bonded hydrogen with a compound containing aliphatic unsaturation, said addition being referred to as hydrosilation, comprising using, as a platinum hydrosilation catalyst, a complex represented by the formula:

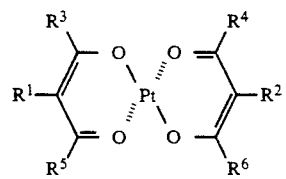

wherein $R^1$ and $R^2$ independently represent hydrogen, an alkyl group, or an aryl group, $R^3$, $R^4$, $R^5$, and $R^6$ independently represent an alkyl group, an aryl group, or an alkoxy group. The invention also includes novel compositions, capable of undergoing hydrosilation, containing the platinum complexes disclosed herein. An important application of the process and compositions of the invention is as a visible light curable impression material for dental applications.

6 Claims, No Drawings

RADIATION ACTIVATED HYDROSILATION REACTION

This is a division of application Ser. No. 07/354,629 filed May 19, 1988, now abandoned.

BACKGROUND OF THE INVENTION

1. Field of the Invention

This invention relates to a hydrosilation process involving the reaction of a compound containing silicon-bonded hydrogen with a compound containing aliphatic unsaturation in the presence of actinic radiation. The invention further relates to polysiloxane compositions, prepared by said process, which compositions are useful for preparing dental impressions, adhesives, release liners, gaskets, caulking materials, and coatings.

2. Discussion of the Art

Numerous patents teach the use of various complexes of cobalt, rhodium, nickel, palladium, or platinum as catalysts for accelerating the thermally-activated addition reaction (hydrosilation) between a compound containing silicon-bonded hydrogen and a compound containing aliphatic unsaturation. For example, U.S. Pat. No. 4,288,345 (Ashby et al) discloses as a catalyst for hydrosilation reactions a platinum-siloxane complex. U.S. Pat. No. 3,470,225 (Knorre et al) discloses production of organic silicon compounds by addition of a compound containing silicon-bonded hydrogen to organic compounds containing at least one non-aromatic double or triple carbon-to-carbon bond using a platinum compound of the empirical formula $PtX_2(RCOCR'COR'')_2$ wherein X is halogen, R is alkyl, R' is hydrogen or alkyl, and R'' is alkyl or alkoxy. The catalysts disclosed in the foregoing patents are characterized by their high catalytic activity. Other platinum complexes for accelerating the aforementioned thermally-activated addition reaction include a platinacyclobutane complex having the formula $(PtCl_2—C_3H_6)_2$ (U.S. Pat. No. 3,159,662, Ashby); a complex of a platinous salt and an olefin (U.S. Pat. No. 3,178,464, Pierpoint); a platinum-containing complex prepared by reacting chloroplatinic acid with an alcohol, ether, aldehyde, or mixtures thereof (U.S. Pat. No. 3,220,972, Lamoreaux); a platinum compound selected from trimethylplatinum iodide and hexamethyldiplatinum (U.S. Pat. No. 3,313,773, Lamoreaux); a hydrocarbyl or halohydrocarbyl nitrile-platinum (II) halide complex (U.S. Pat. No. 3,410,886, Joy); a hexamethyl-dipyridinediplatinum iodide (U.S. Pat. No. 3,567,755, Seyfried et al); a platinum curing catalyst obtained from the reaction of chloroplatinic acid and a ketone having up to fifteen carbon atoms (U.S. Pat. No. 3,814,731, Nitzsche et al); a platinum compound having the general formula $(R')PtX_2$ where R' is a cyclic hydrocarbon radical or substituted cyclic hydrocarbon radical having two aliphatic carbon-carbon double bonds, and X is a halogen or alkyl radical (U.S. Pat. No. 4,276,252, Kreis et al); platinum alkyne complexes (U.S. Pat. No. 4,603,215, Chandra et al.); platinum alkenylcyclohexene complexes (U.S. Pat. No. 4,699,813, Cavezzan); and a colloidal hydrosilation catalyst provided by the reaction between a silicon hydride or a siloxane hydride and a platinum (0) or platinum (II) complex (U.S. Pat. No. 4,705,765, Lewis). Although these platinum complexes and many others are useful as catalysts in processes for accelerating the thermally-activated addition reaction between compounds containing silicon-bonded hydrogen and compounds containing aliphatic unsaturation, processes for promoting the radiation activated addition reaction between these compounds are rare. Platinum complexes that can be used to initiate ultraviolet radiation activated hydrosilation reactions have been disclosed, e.g., platinum azo complexes (U.S. Pat. No. 4,670,531, Eckberg); ($\eta^4$-1,5-cyclooctadiene)diarylplatinum complexes (U.S. Pat. No. 4,530,879, Drahnak); and ($\eta^5$-cyclopentadienyl)-trialkylplatinum complexes (U.S. Pat. No. 4,510,094, Drahnak). Other compositions that are curable by ultraviolet radiation include those described in U.S. Pat. Nos. 4,640,939 and 4,712,092 and in European Patent Application 0238033. However, these patents do not indicate that the platinum complexes disclosed therein would be useful for initiating a visible radiation activated hydrosilation reaction.

Assignee's copending application, U.S. Ser. No. 242,478, filed Sep. 9, 1988, describes a visible radiation activated hydrosilation system. While this catalyst system provides an alternative to UV initiated hydrosilation, several limitations can be cited. First, the system requires both a visible light absorbing sensitizer and a stable UV absorbing photohydrosilation catalyst, for example, an ($\eta^5$ -cyclopentadienyl)trialkyl platinum complex. Second, relatively high concentrations of the platinum catalyst, up to 1000 ppm platinum, are essential for rapid cure in certain systems. Third, these systems have limited depth of cure. Finally, these systems have only a moderately long shelf-life at room temperature.

SUMMARY OF THE INVENTION

In one aspect, this invention provides a process for the actinic radiation-activated addition reaction of a compound containing silicon-bonded hydrogen with a compound containing aliphatic unsaturation, said addition being referred to as hydrosilation, comprising using, as a platinum hydrosilation catalyst, a complex represented by the formula:

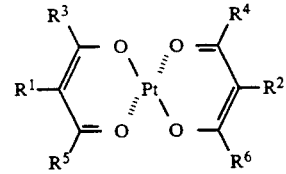

wherein $R^1$ and $R^2$ independently represent hydrogen, an alkyl group, or an aryl group, and $R^3$, $R^4$, $R^5$, and $R^6$ independently represent an alkyl group, an aryl group, or an alkoxy group. Representative examples of suitable Pt(II) β-diketonate complexes include Pt(II) bis(2,4-pentanedionate), Pt(II) bis(2,4-hexanedionate), Pt(II) bis(2,4-heptanedionate), Pt(II) bis(3,5-heptanedionate), Pt(II) bis(1-phenyl-1,3-butanedionate), Pt(II) bis(1,3-diphenyl-1,3-propanedionate), and the like. The process is applicable both to the synthesis of low molecular weight compounds and to the curing of high molecular weight compounds, i.e., polymers, containing unsaturated groups, e.g., —C═C—. For example, the process comprises exposing to actinic radiation, i.e., ultraviolet or visible radiation having a wavelength of about 200 nm to about 800 nm, a composition capable of undergoing hydrosilation comprising:

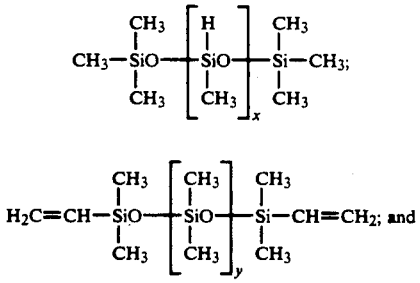

(3) a platinum (II) β-diketonate complex catalyst.

The invention further involves novel compositions, capable of undergoing hydrosilation, containing the platinum complexes disclosed herein.

An important application of the process and compositions of the invention is as a visible light curable impression material for dental applications.

Advantages of the platinum (II) β-diketonate complex in accelerating the actinic radiation-activated addition reaction of compounds containing silicon-bonded hydrogen with compounds containing aliphatic unsaturation include the following:

(1) the reaction composition will not react prematurely or readily in the absence of actinic radiation;

(2) because heat is not required, the addition reaction can be carried out on the surface of a heat-sensitive substrate without adversely affecting the substrate;

(3) actinic radiation curing requires less energy than does thermal curing;

(4) because visible radiation can be used, the reaction can be conducted so as to provide greater safety than is possible with compositions that require ultraviolet radiation;

(5) the composition allows the cure of unusually thick sections of material; and (6) low levels of catalyst can be used.

DETAILED DESCRIPTION

As used in this application, the term "compound", unless indicated otherwise, is a chemical substance which has a particular molecular identity or is made of a mixture of such substances, e.g., polymeric substances. The term "hydrosilation" means the addition of organosilicon compounds containing silicon-bonded hydrogen to a compound containing an aliphatic multiple bond, and in the hydrosilation process described in this application, it refers to those processes in which platinum-containing catalysts are used to effect the addition of an organosilicon compound having a silicon-bonded hydrogen atom to an aliphatically unsaturated compound having either olefinic or acetylenic unsaturation.

In a preferred embodiment of the invention, the platinum complex is a platinum (II) β-diketonate complex having the formula:

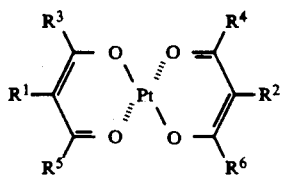

wherein $R^1$ and $R^2$ independently represent hydrogen, an alkyl group, preferably having 1 to 10 carbon atoms, or an aryl group, preferably having 6 to 18 carbon atoms, and $R^3$, $R^4$, $R^5$, and $R^6$ independently represent an alkyl group, preferably having 1 to 10 carbon atoms, an aryl group, preferably having 6 to 18 carbon atoms, or an alkoxy group, preferably having 1 to 10 carbon atoms.

The alkyl, aryl, or alkoxy groups represented by $R^1$, $R^2$, $R^3$, $R^4$, $R^5$, and $R^6$ can be unsubstituted or substituted, said substituents, if any, not interfering in a hydrosilation reaction. The groups can be straight-chain, branched-chain, and, if sufficiently large, cyclic.

Turning now to the reactants to be used in the radiation-activated addition reaction, compounds containing aliphatic unsaturation which are useful in the present invention have olefinic or acetylenic unsaturation. These compounds are well-known in the art of hydrosilation and are disclosed in such patents as U.S. Pat. No. 3,159,662 (Ashby), U.S. Pat. No. 3,220,972 (Lamoreaux)), and U.S. Pat. No. 3,410,886 (Joy), which disclosures of said compounds are incorporated herein by reference. In instances where these unsaturated compounds contain elements other than carbon and hydrogen, it is preferred that these elements be either oxygen, nitrogen, silicon, a halogen, or a combination thereof. The aliphatically unsaturated compound can contain one or more carbon-to-carbon multiple bonds. Representative examples of the aliphatically unsaturated hydrocarbons which can be employed include mono-olefins, for example, ethylene, propylene, and 2-pentene, diolefins, for example, divinylbenzene, butadiene, and 1,5-hexadiene, cycloolefins, for example, cyclohexene and cycloheptene, and monoalkynes, for example, acetylene, propyne, and 1-butene-3-yne. The aliphatically unsaturated compounds can have up to 20 to 30 carbon atoms, or more.

Oxygen-containing aliphatically unsaturated compounds can also be used, especially where the unsaturation is ethylenic, such as methylvinyl ether, divinylether, phenylvinyl ether, monoallyl ether of ethylene glycol, allyl aldehyde, methylvinyl ketone, phenylvinyl ketone, acrylic acid, methacrylic acid, methyl acrylate, allyl acrylate, methyl methacrylate, allyl methacrylate, vinylacetic acid, vinyl acetate, and linolenic acid. Heterocyclic compounds containing aliphatic unsaturation in the ring, such as dihydrofuran, and dihydropyran, are also suitable for the present invention.

Halogenated derivatives of the previously mentioned aliphatically unsaturated compounds can be employed, including acyl chlorides as well as compounds containing a halogen substituent on a carbon atom other than a carbonyl carbon atom. Such halogen-containing compounds include, for example, vinyl chloride, and the vinylchlorophenyl esters.

Unsaturated compounds containing nitrogen substituents such as acrylonitrile, N-vinylpyrrolidone, alkyl cyanide, nitroethylene, etc., are also useful in the practice of the present invention.

Other unsaturated compounds useful in the practice of the present invention include polymers containing aliphatic unsaturation, such as the polyester resins prepared from polybasic saturated or unsaturated acids with polyhydric unsaturated alcohols, and the polyester resins prepared by reacting unsaturated polybasic acids with saturated polyhydric alcohols.

A particularly useful type of unsaturated compound which can be employed in the practice of the present invention is that containing silicon, such as those compounds commonly referred to as organosilicon monomers or polymers. These unsaturated organosilicon compounds have at least one aliphatically unsaturated organic radical attached to silicon per molecule. The aliphatically unsaturated organosilicon compounds include silanes, polysilanes, siloxanes, silazanes, as well as monomeric or polymeric materials containing silicon atoms joined together by methylene or polymethylene groups or by phenylene groups.

Preferred among the aliphatically unsaturated organosilicon compounds useful in the present invention are the monomeric silanes having the empirical formula:

$$R_b^7 R_c^8 SiX_{(4-b-c)} \quad \text{(II)}$$

the cyclopolysiloxanes having the empirical formula:

$$(R^7 R^8 SiO)_d \quad \text{III}$$

and the polyorganosiloxanes having the empirical formula:

$$R_e^7 R_f^8 SiO_{(4-e-f)/2} \quad \text{IV}$$

wherein
$R^7$ represents a monovalent aliphatic unsaturated hydrocarbyl group,
$R^8$ represents a monovalent saturated hydrocarbyl group,
X represents a hydrolyzable group,
b represents an integer from 1 to 4, inclusive,
c represents zero or an integer from 1 to 3, inclusive, the sum of b and c being 1 to 4,
d represents an integer from 3 to 18, inclusive,
e represents a number having a value of 0.0001 to 1, inclusive, and
f represents zero or a number such that the sum of e and f is equal to 1 to 2, inclusive.

Monovalent aliphatic unsaturated hydrocarbyl groups represented by R include alkenyl, for example, vinyl, propenyl, isopropenyl, 3-butenyl, and 5-hexenyl. Groups represented by R: include, for example, alkyl groups, such as methyl, ethyl, and pentyl; cycloalkyl groups, such as cyclopentyl and cyclohexyl; aryl groups such as phenyl and tolyl; aralkyl groups, such as benzyl and phenylethyl; halogenated hydrocarbyl groups, such as haloalkyl, e.g., chloromethyl, trichloromethyl, and 3,3,3-trifluoropropyl, and haloaryl, e.g., chlorophenyl. Hydrolyzable groups represented by X include, for example, halogen groups such as chloro, bromo, and iodo, alkoxy groups such as methoxy, ethoxy, and phenoxy, and acyloxy groups such as acetoxy, propionoxy, and benzoyloxy. A hydrolyzable group is one which undergoes a displacement reaction with water.

In one particularly preferred embodiment of the process of the invention, the compound containing aliphatic unsaturation is an aliphatically unsaturated polyorganosiloxane represented by the general formula:

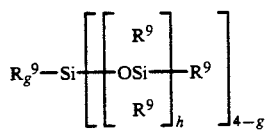

V wherein each $R^9$ can be the same or different and represents a non-halogenated or halogenated ethylenically-unsaturated group, preferably having from 2 to 18 carbon atoms, such as, for example, vinyl, propenyl, chlorovinyl, and 5-hexenyl, a non-halogenated or halogenated alkyl group, preferably having from 1 to 18 carbon atoms, such as, for example, methyl, ethyl, propyl, hexyl, octyl, dodecyl, octadecyl, trichloromethyl, and 3,3,3-trifluoropropyl, a non-halogenated or halogenated cycloalkyl group, preferably having from 3 to 12 carbon atoms, such as, for example, cyclopentyl and cyclohexyl, or an aryl group, preferably having 6 to 18 carbon atoms, such as, for example, phenyl, naphthyl, tolyl, and xylyl, at least 70% of all $R^9$ groups being methyl groups, but no more than 10% of all $R^9$ groups being vinyl or other alkenyl, e.g., having 3 to 18 carbon atoms, and at least one of the $R^9$ groups being vinyl or other alkenyl, e.g., having 3 to 18 carbon atoms;

h represents a number having a value from 1 to about 3000;

g represents 0, 1, 2, or 3.

The reactant containing the silicon-hydrogen linkage can be a polymeric compound or a compound that is not polymeric. These compounds are well-known in the art and are disclosed in the patents which describe the aliphatically unsaturated reactant, i.e., Ashby, U.S. Pat. No. 3,159,662; Lamoreaux, U.S. Pat. No. 3,220,972; and Joy, U.S. Pat. No. 3,410,886. The reactant containing the silicon-hydrogen linkage should contain at least one silicon-bonded hydrogen atom per molecule, with no more than three hydrogen atoms attached to any one silicon atom.

Some classes of compounds having a silicon-bonded hydrogen atom which can be used in the invention are organosilanes having the empirical formula $$H_j SiR_k^{10} X_{(4-j-k)} \quad \text{VI}$$

organocyclopolysiloxanes having the empirical formula $$(HR^{10}SiO)_d \quad \text{VII}$$

and organohydrosiloxane polymers or copolymers having the empirical formula $$R_f^{10} SiH_e O_{(4-e-f)/2} \quad \text{VIII}$$

wherein
$R^{10}$ represents an organic group, preferably selected from the group consisting of monovalent hydrocarbyl groups, and halogenated monovalent hydrocarbyl groups,
j represents the integer 1, 2, or 3,
k represents zero or an integer from 1 to 3, inclusive, the sum of j and k being equal to 1 to 4,
X, d, e and f are as defined above for formulas II, III, and IV.

Among the groups represented by $R^{10}$ include, for example, alkyl groups having 1 to 18 carbon atoms, e.g., methyl, ethyl, propyl, octyl, and octadecyl, cycloalkyl groups having 3 to 12 ring carbon atoms, e.g., cyclohexyl and cycloheptyl, aryl groups having 6 to 18 carbon atoms, e.g., phenyl, naphthyl, tolyl, and xylYl, and combinations of alkyl and aryl groups, e.g., aralkyl groups, such as, benzyl and phenylethyl, and halo-substituted groups thereof, e.g., chloromethyl, chlorophenyl, and dibromophenyl. Preferably, the $R^{10}$ group is methyl or both methyl and phenyl. The $R^{10}$ group can also be an unsaturated aliphatic group having 1 to 18 carbon atoms, such as alkenyl or cycloalkenyl, e.g., vinyl, allyl and cyclohexenyl. When the $R^{10}$ group is a group with aliphatic unsaturation, the silicon compound containing silicon-hydrogen linkages can be reacted with itself to form a polymer.

Among the inorganic compounds which contain silicon-bonded hydrogen atoms and which are useful as reactants in the process of the present invention are included, for example, trichlorosilane, dibromosilane, pentachlorodisilane, pentachlorodisiloxane, and heptachlorotrisilane.

A preferred compound having silicon-bonded hydrogen useful in this invention is a polyorganohydrosiloxane having the general formula:

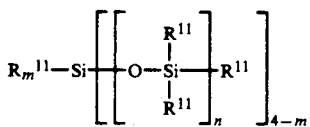

IX wherein
each $R^{11}$ can be the same or different and represents hydrogen, an alkyl group, preferably having 1 to 18 carbon atoms, a cycloalkyl group, preferably having 3 to 12 carbon atoms, or a phenyl group, at least one but not more than one-half of all the $R^{11}$ groups in the siloxane being hydrogen;
m represents 0, 1, 2, or 3; and
n represents a number having an average value from 1 to about 3000.

The hydrosilation composition useful in the synthesis of low molecular weight compounds by the process of the invention can be prepared by mixing about 0.1 to about 10.0 equivalent weights of the compound having silicon-bonded hydrogen with one equivalent weight of the compound having aliphatic unsaturation and then adding an amount of platinum complex catalyst sufficient to catalyze the reaction. The amount of the catalyst can range from about 5 to about 5000 parts by weight, preferably from about 25 to about 500 parts by weight, per 1,000,000 parts by weight of the total composition.

Known techniques can be used to conduct the hydrofilation reaction. In carrying out a hydrosilation reaction in the practice of this invention, the reactants and catalyst can be introduced into a vessel equipped for stirring, where the mixture is stirred and exposed to actinic radiation until the reaction is complete. If either of the reactants is a solid or is extremely viscous, a solvent can be introduced into the vessel to facilitate uniform mixing of the reactants. Suitable solvents include aromatic hydrocarbons, such as xylene and toluene, aliphatic hydrocarbons, such as hexane and mineral spirits, and halogenated hydrocarbons, such as chlorobenzene and trichloroethane. It is desirable that the solvent be transmissive to actinic radiation. From about 0.1 to about 10 parts of solvent per part by weight of the combined reactants can be used. The resulting reaction product will generally be sufficiently pure for its intended use. However, it may be desirable to remove the solvent if one has been employed.

The hydrosilation compositions useful in the preparation of higher molecular weight cured siloxane polymers by the process of this invention can be prepared by mixing an aliphatically unsaturated polysiloxane and a compound having silicon-bonded hydrogen in such a proportion so as to provide about 0.1 to about 10.0 silicon-bonded hydrogen atoms per unsaturated group, and then adding from about 5 to about 5000 parts by weight, preferably from about 25 to about 500 parts by weight of platinum complex catalyst per 1,000,000 parts by weight of the total composition. The reaction mixture can be mixed, as by stirring, blending, or tumbling, until it is homogeneous.

The thoroughly mixed composition can then be applied to a substrate by any suitable means, such as by spraying, dipping, knife coating, curtain coating, roll coating, or the like, and the coating cured by using conventional techniques for providing actinic radiation. It is preferred that curing be conducted by exposing the coated substrate to radiation having a wavelength of about 200 nm to about 800 nm. Depending on the particular silicone formulation, catalyst, and intensity of the actinic radiation, curing can be accomplished in a period from less than one second to less than 30 minutes. Any radiation source capable of emitting radiation above about 200 nm can be used. Examples of suitable radiation sources include tungsten halogen lamps, xenon arc lamps, mercury arc lamps, incandescent lamps, and fluorescent lamps. Particularly preferred sources of actinic radiation are tungsten halogen, xenon arc, and mercury arc lamps.

Various additives conventionally included in hydrosilation compositions can be included in the curable compositions, depending on the intended purpose of the composition. Fillers and/or pigments, such as chopped fibers, crushed polymers, talc, clay, titanium dioxide, and fumed silica can be added. Soluble dyes, oxidation inhibitors, and/or any material that does not interfere with the catalytic activity of the platinum complex can be added to the composition.

The shelf life of the curable compositions containing the catalyst can be extended by the addition of a conventional catalyst inhibitor. The amount of catalyst inhibitor can vary from about 1 to about 10 times, or more, the amount of platinum complex, depending on the activity of the particular complex used and the shelf life desired for the composition. Greater amounts of inhibitor should be used with the more active complexes, with lesser amounts being used for the less active complexes. Hydrosilation inhibitors are well known in the art and include such compounds as acetylenic alcohols, certain polyolefinic siloxanes, pyridine, acrylonitrile, organic phosphines and phosphites, unsaturated amides, and alkyl maleates.

The hydrosilation compositions of this invention can be applied to the surface of any solid substrate for a variety of purposes. Examples of such substrates include paper, cardboard, wood, cork, plastic such as polyester, nylon, polycarbonate, etc., woven and nonwoven fabric such as cotton, polyester, nylon, etc., metal, glass, and ceramic.

It is often advantageous to prime the surface of nonporous substrates to which the hydrosilation composition is to be applied to improve the adhesion of the composition to the substrate. Many primers and priming techniques (e.g., corona treatment) are described in the art and should be chosen on the basis of the substrate to be used. For example, the epoxy-functional siloxanes as taught in U.S. Pat. No. 4,243,718 (Murai et al) are useful for priming the surface of plastic films such as polyester and polyvinylchloride.

In the following examples, compositions were prepared by combining and mixing a vinyl functional polysiloxane, a hydride functional polysiloxane, and a platinum complex catalyst. Compositions were evaluated for cure speed in the following manner. Molds made from 1.5 mm thick "Teflon" sheet with a 6 mm diameter hole through the sheet were clamped to clean glass slides so that the central axis of the hole in the mold was normal to the glass slide. The hole was filled with a sample of the composition being evaluated. Either a "Visilux" 2 dental curing light with a light output between 400 and 500 nm or a "Caulk-Hanovia" ultraviolet curing light with a maximum intensity output of 366 nm was clamped to a ring stand and positioned such that the cylindrical tip of the light source was 5.0 mm above the top of the "Teflon" mold. The sample was centered directly beneath the light tip. The sample was irradiated with the "Visilux" 2 or the "Caulk-Hanovia" light until a tack-free, cohesive silicone polymer was obtained, as determined by means of a metal probe. All samples were tested in duplicate or triplicate.

EXAMPLE 1

A stock composition was prepared by mixing in a glass container 85 parts by weight of a vinyl terminated polydimethylsiloxane having the formula:

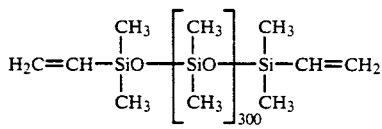

and 15 parts by weight of a compound containing silicon bonded hydrogen having the formula:

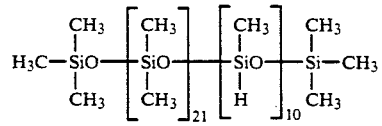

To 10.0 g aliquots of this composition were added varying quantities of a photohydrosilation catalyst selected from Pt(II) bis(2,4-pentanedionate), alternatively known as Pt(II) acetylacetonate, hereinafter referred as Pt(acac)$_2$ and ($\eta^5$-cyclopentadienyl) trimethylreferred herein referred to as CpPtMe$_3$. The formula of Pt(acac)$_2$ is as follows:

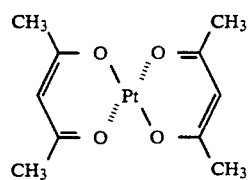

Dichloromethane was used sparingly to promote solubility of the platinum complexes. Samples were irradiated with a "Visilux" 2 visible light source as previously describe,d and the time until gelation of these compositions is recorded in Table I.

TABLE I

| Sample | ppm Pt | Gel time based on catalyst used (sec) | |
|---|---|---|---|
| | | Pt(acac)$_2$ | CpPtMe$_3$ |
| 1 | 12.5 | 54 | — |
| 2 | 25 | 41 | — |
| 3 | 50 | 37 | — |
| 4–5 | 100 | 37 | 190 |
| 6–7 | 200 | 38 | 182 |
| 8–9 | 400 | 38 | 155 |
| 10–11 | 500 | 37 | 145 |
| 12–13 | 750 | 36 | 140 |
| 14–15 | 1000 | 36 | 120 |

The data in Table I show that as little as 0.0025% by weight Pt(acac)$_2$ (12.5 ppm Pt) can provide satisfactory rates of cure. Cure speed is enhanced by increasing the amount of Pt(acac)$_2$ up to 0.01% by weight (50 ppm Pt). Higher concentrations of the catalyst did not improve gel time. In contrast, gel times for composiitons containing CpPtMe$_3$ increase as concentration of catalyst increases, up to at least 1,000 ppm Pt. However, gel times obtained with CpPtMe$_3$ at all concentrations are higher than those obtained with Pt(acac)$_2$.

EXAMPLE 2

In a procedure similar to that described in Example 1, a stock composition was prepared by combining 97.5 parts by weight of a vinyl terminated polydimethylsiloxane having the formula:

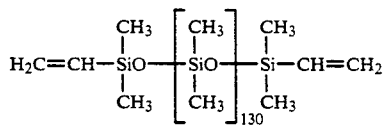

and 2.5 parts by weight of a compound containing silicon-bonded hydrogen having the formula:

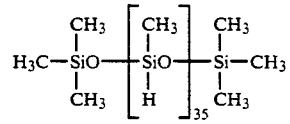

To 10.0 g aliquots of this composition were added varying quantities of a photohydrosilation catalyst selected from Pt(acac)$_2$, CpPtMe$_3$, and [$\eta^5$-(phenyldimethylsilyl)cyclopentadienyl]-trimethylplatinum, hereinafter referred to as PhMe$_2$SiCpPtMe$_3$. Samples were irradiated as previously described in Example 1, and the time until gelation of these compositions is recorded in Table II.

TABLE II

| Sample | ppm Pt | Gel time based on catalyst used (sec) | | |
|---|---|---|---|---|
| | | Pt(acac)$_2$ | CpPtMe$_3$ | PhMe$_2$SiCpPtMe$_3$ |
| 1–3 | 10 | 135 | 240 | 210 |
| 4–6 | 25 | 97 | 184 | 143 |
| 7–9 | 50 | 84 | 110 | 85 |
| 10–12 | 100 | 117 | 107 | 75 |
| 13–15 | 200 | 137 | 88 | 65 |
| 16–18 | 500 | 145 | 68 | 56 |
| 19–21 | 1000 | 175 | 65 | 48 |

The data in Table II show that the rate of cure using the catalysts CpPtMe$_3$ and PhMe$_2$SiCpPtMe$_3$ increases with increasing catalyst concentration up to at least 1000 ppm Pt, whereas the optimum cure rate using Pt(acac)₂ is achieved at a level of 50 ppm Pt. At a level of 50 ppm Pt, Pt(acac)₂ is superior to CpPtMe₃ and roughly equivalent to PhMe₂SiCpPtMe₃.

EXAMPLE 3

To 5.0 g aliquots of the stock composition of Example 1 were added varying quantities of one of the following platinum compounds: Pt(II) bis(2,4-pentanedionate), alternatively known as Pt(II) acetylacetonate or Pt(acac)₂, Pt(II) bis(1-phenyl-1,3-butanedionate),, alternatively known as Pt(II) benzoylacetonate or Pt(BA)₂, Pt(II) bis(1,3-diphenyl-1,3-propanedionate), alternatively known as Pt(II) dibenzoylmethane or Pt(DBM)₂, and Pt(II) bis(1,1,1,5,5,5-hexafluoro-2,4-pentandionate), alternatively known as Pt(HFA)₂. The formula of each derivative is as follows:

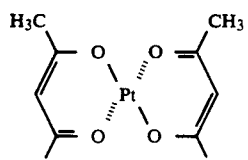

Pt(acac)₂

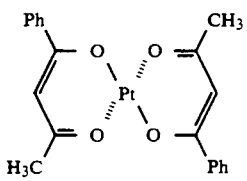

Pt(BA)₂

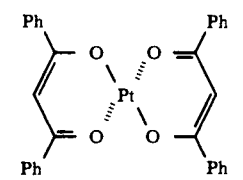

Pt(DBM)₂

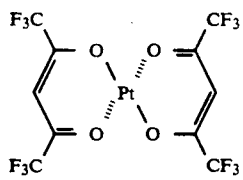

Pt(HFA)₂

In the foregoing formulas, Ph represents the radical

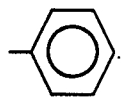

Dichloromethane was used sparingly to promote solubility of the platinum complexes. Samples were irradiated with a "Visilux" 2 visible light source as previously described, and the times until gelation of these compositions are recorded in Table III.

TABLE III

| Sample | ppm Pt | Pt(acac)₂ | Pt(BA)₂ | Pt(DBM)₂ | Pt(HFA)₂ |
|---|---|---|---|---|---|
| 1-4 | 6 | 76 | 72 | 130 | 83 |
| 5-8 | 12.5 | 52 | 51 | 60 | 65 |
| 9-12 | 25 | 48 | 50 | 88 | 95 |
| 13-16 | 50 | 38 | 40 | 82 | 100 |

Gel time based on catalyst used (sec)

The data of Table III show that (1) all four catalyst systems are capable of promoting hydrosilation; (2) Pt(acac)₂ and Pt(BA)₂ are more effective catalysts than Pt(DBM)₂ and Pt(HFA)₂; and (3) as little as 6 ppm Pt can provide satisfactory gel time.

EXAMPLE 4

To 10.0 g aliquots of the stock composition of Example 2 were added varying quantities of Pt(acac)₂ as a photohydrosilation catalyst. Samples were irradiated with a source of ultraviolet light as previously described, and the time until gelation of these compositions is recorded in Table IV.

TABLE IV

| Sample | ppm Pt | Gel time (sec) |
|---|---|---|
| 1 | 25 | 460 |
| 2 | 50 | 440 |
| 3 | 200 | 480 |
| 4 | 500 | 520 |

The data in Table IV show that Pt(acac)₂ is also a useful catalyst for actinic radiation activated hydrofilation at wavelengths of less than 400 nm and that the optimum catalyst concentration is about 50 ppm Pt.

EXAMPLE 5

Seven silicone formulations were prepared from the vinyl terminated polydimethylsiloxane and silicon-bonded hydrogen compound described in Example 1 such that the amount of hydride functional silicone ranged from 0 to 25% by weight of the compositions. To each formulation was added 0.02% by weight of Pt(acac)₂ (100 ppm Pt), and the resulting compositions were mixed until homogeneous. Compositions containing 0.10% by weight of Pt(acac)₂ (500 ppm Pt) were prepared in a similar fashion. Samples were irradiated with a "Visilux" 2 visible light source as previously described, and the time until gelation of these compositions is recorded in Table V.

TABLE V

| Sample | ppm Pt | Hydride (% by wt) | Gel time (sec) |
|---|---|---|---|
| 1 | 100 | 0.0 | no cure |
| 2 | 100 | 2.5 | 71 |
| 3 | 100 | 5.0 | 56 |
| 4 | 100 | 10.0 | 36 |
| 5 | 100 | 15.0 | 36 |
| 6 | 100 | 20.0 | 33 |
| 7 | 100 | 25.0 | 33 |
| 8 | 500 | 0.0 | no cure |
| 9 | 500 | 2.5 | 62 |
| 10 | 500 | 5.0 | 52 |
| 11 | 500 | 10.0 | 36 |
| 12 | 500 | 15.0 | 34 |
| 13 | 500 | 20.0 | 33 |
| 14 | 500 | 25.0 | 33 |

The data in Table V show that at a given catalyst concentration, the rate of cure increases with increasing concentrations of the hydride functional silicone (crosslinking agent) up to a level of 20% by weight.

EXAMPLE 6

To aliquots of a stock composition prepared as described in Example 1 were added quantities of $Pt(acac)_2$ varying from 0.005 to 0.1% by weight. Samples were evaluated for depth of cure as a function of irradiation time. The source of radiation was a "Visilux" 2 visible light source as previously described. A sample was transferred to a clear, disposable polyethylene pipet having an inside diameter of 6 mm and a length of approximately 65 mm. The pipet was fitted to a reusable black plastic sheath such that the modified pipet was fully surrounded, with the exception of the circular opening. The "Visilux" 2 visible light source was placed such that the tip of the light source was flush with the opening of the pipet, and the sample was irradiated for either 30, 60, 90, or 120 seconds. Following irradiation, the modified pipet was removed from the sheath, opened with a razor blade, and the cured rubbery mass was separated from uncured silicone. Depths of cure are recorded in Table VI.

TABLE VI

| Sample | ppm Pt | Cure depth (mm) based on irradiation time | | | |
|---|---|---|---|---|---|
| | | 30 sec | 60 sec | 90 sec | 120 sec |
| 1-4 | 25 | 25 | 49 | 52 | 58 |
| 5-8 | 50 | 29 | 34 | 53 | 60 |
| 9-12 | 100 | 29 | 34 | 37 | 47 |
| 13-16 | 250 | 19 | 25 | 27 | 31 |
| 17-20 | 375 | 17 | 20 | 22 | 24 |
| 21-24 | 500 | 10 | 11 | 16 | 22 |

Example 6 illustrates that cure depth increases with increasing irradiation time and that lower concentrations of $Pt(acac)_2$ generally allow greater depth of cure. A depth of cure as great as 6 cm was achieved with $Pt(acac)_2$.

EXAMPLE 7

To aliquots of a stock composition prepared as described in Example 2 were added varying quantities of either $Pt(acac)_2$ or $CpPtMe_3$ as a photohydrosilation catalyst. Samples were evaluated for depth of cure essentially as described in Example 6, with the exception that for each sample a glass pipet, wrapped with black tape, extending approximately 200 mm in length, and having one end closed with a rubber septum, was used in place of the modified pipets. Samples were irradiated for 120 seconds with a "Visilux" 2 visible light source as previously described, and the depth of cure was measured immediately after irradiation. The evaluations were repeated. The samples were maintained in the dark for 5 minutes following irradiation before measuring the depth of cure. Results are recorded in Table VII.

TABLE VII

| Sample | Catalyst | ppm Pt | Cure depth (mm) based on irradiation time | |
|---|---|---|---|---|
| | | | immediate | 5 minutes |
| 1-2 | $Pt(acac)_2$ | 5 | 110 | 155 |
| 3-4 | $Pt(acac)_2$ | 10 | 85 | 160 |
| 5-6 | $Pt(acac)_2$ | 25 | 120 | 135 |
| 7-8 | $Pt(acac)_2$ | 50 | 9 | 60 |
| 9-10 | $Pt(acac)_2$ | 100 | 5 | 10 |
| 11-12 | $CpPtMe_3$ | 10 | 0 | 10 |
| 13-14 | $CpPtMe_3$ | 25 | 5 | 15 |
| 15-16 | $CpPtMe_3$ | 50 | 10 | 45 |
| 17-18 | $CpPtMe_3$ | 100 | 10 | 15 |

The data in Table VII show that the use of $Pt(acac)_2$, particularly at low concentrations of catalyst, provides depth of cure far superior to that provided by $CpPtMe_3$.

EXAMPLE 8

To 10.0 g aliquots of the stock composition of Example 2 were added 200 ppm Pt as either $Pt(acac)_2$ or $CpPtMe_3$. The samples were introduced into 4 oz. amber glass bottles, which were then placed in a forced air oven at 50° C. The gel time of the sample containing $CpPtMe_3$ was observed to be 6-7 hours; the gel time of the sample containing $Pt(acac)_2$ was observed to be 24-48 hours. Gel time at room temperature was also measured. The room temperature gel time of a sample containing $CpPtMe_3$ was observed to be 10 days; that of a sample containing $Pt(acac)_2$ was observed to be greater than 150 days. These results show that at temperatures equal to or less than 50° C., the thermal stability, or shelf life, of silicone compositions containing $Pt(acac)_2$ is superior to that of compositions containing $CpPtMe_3$.

EXAMPLE 9

Two compositions analogous to those described in Example 1 containing 0.20% by weight of $Pt(acac)_2$ (990 ppm Pt) were prepared and evaluated for shelf stability at 25° C. and 4° C. Aliquots were withdrawn at intervals and examined for inherent fluidity and gel time upon irradiation with a "Visilux" 2 visible light source as previously described. Results are recorded in Table VIII.

TABLE VIII

| Storage time (days) | Observed fluidity based on storage temperature | | Gel time based on storage temperature (sec) | |
|---|---|---|---|---|
| | 4° C. | 25° C. | 4° C. | 25° C. |
| 0 | Fluid | Fluid | — | 37 |
| 7 | Fluid | Fluid | 38 | 37 |
| 22 | Fluid | Fluid | 34 | 34 |
| 36 | Fluid | Fluid | 35 | 38 |
| 57 | Fluid | Fluid | 37 | 37 |
| 100 | Fluid | Fluid | 37 | 37 |
| 200 | Fluid | Fluid | 37 | 37 |

The data in Table VIII demonstrate that silicone formulations containing $Pt(acac)_2$ exhibit excellent shelf stability at or below room temperature with little or no change in observed irradiation gel time.

EXAMPLE 10

A composition consisting of the following ingredients in the amoutns indicated was prepared:

| Ingredient | Amount (parts by weight) |
|---|---|
| Vinyl siloxane polymer[1] | 82.9 |
| Crosslinking agent[2] | 14.6 |
| $Pt(acac)_2$ | 0.008 |

-continued

| Ingredient | Amount (parts by weight) |
|---|---|
| Fumed silica[3] | 2.5 |

[1] $CH_2=CH-Si(CH_3)_2-[OSi(CH_3)_2]_x-CH=CH_2$
    $x = 1000$
[2] PMC 54, available from Minnesota Mining and Manufacturing Company
[3] "Aerosil" R-972, available from Degussa Corporation The ingredients were introduced into a 250 ml beaker, mixed thoroughly, and transferred to a 50 cc syringe. The syringe was palced under reduced pressure for approximately 30 minutes to remove bubbles from the composition.

A thin film of the foregoing composition was coated by means of a brush onto a single quadrant of a full arch clear plastic dental impression tray. The partially coated tray was placed directly under a GE 4001 12 V automobile headlight at a distance of approximately six inches. The smple was irradiated until the coated film was no longer fluid (approximately five minutes). The surface of the film was slightly tacky. The film tightly adhered to the tray.

The composition described in this example does not require a solvent; accordingly, in contrast to currently available dental impression tray adhesives, solvent removal is unnecessary.

EXAMPLE 11

A compositon consisting of the following ingredients in the amounts indicated was prepared:

| Ingredient | Amount (parts by weight) |
|---|---|
| Vinyl siloxane polymer[1] | 78.6 |
| Crosslinking agent[2] | 13.9 |
| Pt(acac)$_2$ | 0.008 |
| Fumed silica[3] | 7.5 |
| FD & C Blue Lake #2 Dye (Warner-Jenkinson) | 0.016 |

[1] $CH_2=CH-Si(CH_3)_2-[OSi(CH_3)_2]_x-CH=CH_2$
    $x = 300$
[2] PMC 54, available from Minnesota Mining and Manufacturing Company
[3] "Aerosil" R-972, available from Degussa Corporation The ingredients were introduced into a 250 ml beaker, mixed thoroughly until a homogeneous blue mixture was obtained, and transferred to a 50 cc syringe. The syringe was placed under reduced pressure for approximately 30 minutes to remove bubbles from the composition.

The mixture was introduced into a transparent full arch impression tray, one quadrant of which had been previously coated and irradiated according to the procedure of Example 10. In addition, another sample of the formulation was applied as a thin coat to the artificial teeth and gums of a typodont to ensure complete coverage of the dentition. The coated typodont was then placed firmly into the filled impression tray. The tray was irradiated for approximately 5 minutes per quandrant with a "Visilux" 2 visible light source as previously described. When the impression tray was removed from the typodont, it was observed that a fully intact rubbery mass that represented a detailed impression of the dentition was formed. The quadrant that had been pretreated with the composition of Example 10 remained fully bonded to the clear tray, whereas the untreated quandrant exhibited debonding of the cured composition from the tray, thus implicating the need for the tray adhesive of Example 10.

A casting of the impression was prepared by transferring a freshly prepared sample of die stone (Modern Materials, St. Louis, Missouri) to the rubbery composition described in this example. The stone was allowed to set for one hour and then removed from the silicone impression material. The resulting stone casting was found to give a detailed reproduction of the typodont dentition.

EXAMPLE 12

A composition consisting of the following ingredients in the amounts indicated was prepared:

| Ingredient | Amount (parts by weight) |
|---|---|
| Vinyl siloxane polymer[1] | 78.6 |
| Crosslinking agent[2] | 13.9 |
| Pt(acac)$_2$ | 0.008 |
| Fumed silica[3] | 7.5 |

[1] $CH_2=CH-Si(CH_3)_2-[OSi(CH_3)_2]_x-CH=CH_2$
    $x = 300$
[2] PMC 54, available from Minnesota Mining and Manufacturing Company
[3] "Aerosil" R-972, available from Degussa Corporation The ingredients were introduced into a 250 ml beaker, mixed thoroughly, and transferred to a 50 cc syringe. The syringe was placed under reduced pressure for approximately 30 minutes to remove bubbles from the composition.

The foregoing composition was introduced into a mold for preparing a gasket. The mold was placed directly under a GE 4001 12 V automobile headlight at a distance of approximately six inches. The sample was irradiated until the composition was fully cured (approximately three minutes) The surface of the gasket was tack-free.

EXAMPLE 13

This example illustrates the release characteristics of coatings prepared with the compositions of this invention. To a 30.0 g aliquot of the stock composition of Example 2 was added 12 mg of Pt(acac)$_2$ (200 ppm Pt). The composition was coated on super calendered Kraft paper at a coating weight of 1 to 2 g/m$^2$ and cured by irradiation in a PPG processor that advanced the sample at a rate of 50 cm/sec under two medium pressure mercury lamps emitting 120 watts of radiation per centimeter of lamp length and subsequent heating in a circulating air oven to 125° C. for 2 minutes. The use of Pt(HFA)$_2$ in place of Pt(acac)$_2$ allowed a lower subsequent heating temperature of 100° C. Similarly coated samples that were not exposed to radiation did not cure when heated at 125° C. or 150° C.

The release value of the cured silicone coating was determined by the following procedure: A heptane-isopropyl alcohol solution of pressure sensitive adhesive comprising isooctyl acrylate (95.5% by weight)-acrylic acid (4.5% by weight) copolymer, as described in Example 5 of U.S. Pat. No. Re. 24,906, incorporated herein by reference, was applied to the cured silicone coating and dried for 5 minutes at 70° C. in a circulating air oven to give a dry coating weight of 32 g/m$^2$. A biaxially oriented film of polyethylene terephthalate (PET) (38 micrometers thick) was pressed against the surface of the coating to produce a laminate consisting of a pressure-sensitive adhesive tape and a silicone-coated substrate. The laminate was cut into 2.5×25 cm strips. An average value of 15 g per 2.5 cm of width was measured to be the force required to pull the PET film with adhesive attached thereto (i.e., a pressure-sensitive adhesive, tape) away from the silicone-coated substrate at an angle of 180° and a pulling speed of 230 cm/min.

The readhesion value of the pressure-sensitive tapes was determined by the following procedure: The pressure-sensitive tapes, as removed from the silicone coated surface, were applied to the surface of a clean glass plate. An average value of 1400 g per 2.5 cm of width was measured to be the force required to pull the tape from the glass surface at an angle of 180° and a pulling speed of 230 cm/min. A control readhesion value was obtained for the pressure-sensitive tape by applying the tape, which had not been placed in contact with a silicone-coated surface, to a clean glass plate and measuring the force required to remove the tape from the plate. The control readhesion value was 1500 g per 2.5 cm of width.

EXAMPLE 14

This example illustrates the preparation of a silicone-based pressure-sensitive adhesive tape from a composition of this invention. A mixture of the following three ingredients was prepared:

(1) 13.6 g of a dimethylvinylsiloxy endblocked polydimethylsiloxane containing an average of 25.1 dimethylsiloxane units per molecule;

(2) 25.6 g of a dimethylhydrogensiloxy endblocked polydimethylsiloxane containing an average of 28.7 dimethylsiloxane units per molecule; and (3) 100.0 g of a 60 percent by weight solution in xylene of a resinous organosiloxane copolymer comprising $CH_3SiO_{1/2}$, $SiO_{5/2}H$ and $SiO_{4/2}$ units in a ratio of 41.6 : 10.5 : 47.6. The copolymer exhibited a number average molecular weight, determined by gel permeation chromatography, of about 2600 and a dispersity index of 2.6.

The mixture was stripped of volatile material by heating at 65° C. under less than 0.5 mm of Hg pressure on a rotary evaporator. To the resulting viscous mixture were added 0.80 g of 1,3,5,7-tetravinyltetramethylcyclotetrasiloxane, 2.0 g of toluene, and 100 mg of $Pt(acac)_2$. The composition was knife coated at a thickness of 0.05 mm on a 0.05 mm thick polyethylene terephthalate film, and the coating was cured by initially irradiating in a PPG processor that advanced the sample at a rate of 50 cm/sec under two medium pressure mercury lamps emitting 120 watts of radiation per centimeter of lamp length and subsequently heating in a circulating air oven at 100° C. for 5 minutes. The properties of the tape so obtained were determined in the following manner.

Adhesion was determined essentially according to the procedure described in ASTM D-3330 (1983). Strips of the tape 2.54 cm wide and approximately 25 cm long were adhered to a glass surface using a 2.04 kg rolled weight. An average value of 1600 g per 2.5 cm of width was measured to be the force required to pull the adhesive tape away from the glass surface at an angle of 180° and a pulling speed of 230 cm/min.

Shear strength was determined essentially according to the procedure described in ASTM D-3654 (1982). Specimens 1.27 cm wide and approximately 8 cm long were adhered to a bright annealed steel surface with an overlap area of 1.27 cm by 1.27 cm. The samples were suspended vertically and maintained at a temperature of 70° C. for one hour. A 1 kg weight was suspended from the free end of each specimen, and an average of 200 minutes was measured as the elapsed time before the adhesive bond failed while being maintained at a temperature of 70° C. The test was repeated at room temperature, and an average holding time exceeding 10,000 minutes was measured.

The tack of the adhesive tape was measured qualitatively by touching the cured adhesive with a finger. Tack was judged to be moderate.

EXAMPLE 15

This example illustrates the preparation of a conformable coating for electronic components using a composition of this invention. A composition consisting of the following ingredients in the amounts indicated was prepared:

| Ingredient | Amount (parts by weight) |
|---|---|
| Vinyl siloxane polymer[1] | 54.2 |
| Crosslinking agent[2] | 30.8 |
| Pt(acac)2 | 0.008 |
| Fumed silica[3] | 15.0 |

[1] $CH_2=CH-Si(CH_3)_2-[OSi(CH_3)_2]_x-CH=CH_2$
 $x = 130$
[2] PMC 54, available from Minnesota Mining and Manufacturing Company
[3] "Quso", available from Degussa Corporation The ingredients were introduced into a 250 ml beaker, mixed thoroughly, and transferred to a 50 cc syringe. The syringe was placed under reduced pressure for approximately 30 minutes to remove bubbles from the composition.

The composition was applied to an integrated circuit board measuring 2 inches by 2 inches in sufficient quantity to provide a coating approximately 1 mm in thickness. The coating was irradiated with a "Visilux" 2 visible light source as previously described for approximately 4 minutes to provide a tough, elastomeric, transparent coating that adhered well to the circuit board.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A hydrosilation process which comprises reacting a composition comprising a compound having aliphatic unsaturation and a compound containing at least one silicon-bonded hydrogen atom and not havng more than three hydrogen atoms attached to any one silicon atom, in the presence of a platinum (II) β-diketonate complex catalyst, wherein said reaction is carried out by means of exposing said composition to actinic radiation having a wavelength of about 200 nm to about 800 nm.

2. The process of claim 1, wherein the platinum complex catalyst is represented by the formula:

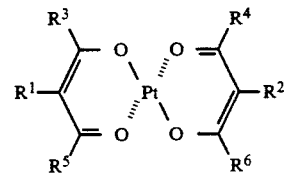

wherein $R^1$ and $R^2$ independently represent hydrogen, an alkyl group, or an aryl group, and $R^3$, $R^4$, $R^5$, and $R^6$ independently represent an alkyl group, an aryl group, or an alkoxy group.

3. The process of claim 1, wherein the composition comprises from 0.1 to 10.0 equivalent weights of the compound having silicon-bonded hydrogen per equivalent weight of the compound having aliphatic unsaturation, and, per 1,000,000 parts by weight of the total composition, from about 5 to about 5,000 parts by weight of the platinum complex catalyst.

4. The process of claim 1, wherein the compound containing aliphatic unsaturation is a polyorganosiloxane having the general formula:

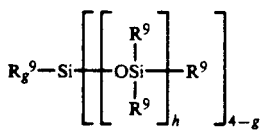

wherein
each $R^9$ independently represents a non-halogenated or halogenated ethylenically-unsaturated group, a non-halogenated or halogenated alkyl group or cycloalkyl group, or an aryl group, at least 70% of all $R^9$ groups being methyl groups, but no more than 10% of all $R^9$ groups being vinyl or other alkenyl, and at least one of the $R^9$ radicals being vinyl or other alkenyl, h represents a number having a value from about 1 to about 3000, and g represents 0, 1, 2, or 3.

5. The process of claim 1, wherein the compound containing silicon-bonded hydrogen is a polyorganohydrosiloxane having the general formula:

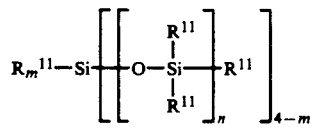

wherein
each $R^{11}$ independently represents an alkyl group, a cycloalkyl group, a phenyl group, a hydroxyalkyl group, a (polyalkoxy)alkyl group, or hydrogen, at least one but no more than 50% of all $R^{11}$ groups being hydrogen, m represents 0, 1, 2 or 3, and n represents a number having an average value from about 1 to about 3000.

6. The process of claim 1, wherein the compound having aliphatic unsaturation is one having olefinic unsaturation.

* * * * *

UNITED STATES PATENT AND TRADEMARK OFFICE
CERTIFICATE OF CORRECTION

PATENT NO. : 5,145,886

DATED : September 8, 1992

INVENTOR(S) : Oxman et al.

It is certified that error appears in the above-indentified patent and that said Letters Patent is hereby corrected as shown below:

Col. 5, line 41, "R" should be --$R^7$--.

Col. 5, line 43, "R:" should be --$R^8$--.

Col. 6, line 65, "xylYl" should be --xylyl--.

Col. 7, line 21, "$R_m^{11}$" should be --$R^{11}_m$--.

Col. 7, lines 47/48, "hydrofilation" should be --hydrosilation--.

Col. 9, lines 38/39, "silicon bonded" should be --silicon-bonded--.

Col. 9, lines 52/53, "trimethylreferred" should be --trimethylplatinum, hereinafter referred--.

Col. 9, line 67, "describe,d" should be --described,--.

Col. 12, line 32, "hydrofilation" should be --hydrosilation--.

Col. 16, line 34, "minutes) The" should be --minutes). The--.

Col. 16, line 48, "oven to 125°C" should be --oven at 125°C--.

UNITED STATES PATENT AND TRADEMARK OFFICE
CERTIFICATE OF CORRECTION

PATENT NO. : 5,145,886
DATED     : September 8, 1992
INVENTOR(S) : Oxman et al

It is certified that error appears in the above-indentified patent and that said Letters Patent is hereby corrected as shown below:

Col. 17, line 2, "adhesive, tape)" should be --adhesive tape)--.

Signed and Sealed this

Twenty-second Day of March, 1994

*Attest:*

BRUCE LEHMAN

*Attesting Officer*  *Commissioner of Patents and Trademarks*